United States Patent [19]

Lokar

[11] Patent Number: 5,299,935
[45] Date of Patent: Apr. 5, 1994

[54] ORTHODONTIC APPLIANCE

[76] Inventor: Robert R. Lokar, 22110 Orchard Way Ct., Birmingham, Mich. 48010

[21] Appl. No.: 983,811

[22] Filed: Dec. 1, 1992

[51] Int. Cl.$^5$ ................................................. A61C 3/00
[52] U.S. Cl. .......................................... 433/18; 433/21
[58] Field of Search .......................... 433/18, 19, 21, 5

[56] References Cited

U.S. PATENT DOCUMENTS

| 3,525,153 | 8/1970 | Gerber | 433/21 |
| 3,936,938 | 2/1976 | Northcutt | 433/21 |
| 4,424,030 | 1/1984 | Smiley et al. | 433/18 |
| 4,424,031 | 1/1984 | Dahan | 433/18 |
| 4,483,674 | 11/1984 | Schutz | 433/18 X |
| 4,595,361 | 6/1986 | Blechman et al. | |
| 5,022,855 | 6/1991 | Jeckel | 433/18 |
| 5,064,370 | 11/1991 | Jones | |
| 5,087,196 | 2/1992 | Polanco | 433/18 X |

Primary Examiner—Gene Mancene
Assistant Examiner—Nicholas D. Lucchesi

[57] ABSTRACT

An orthodontic appliance (10) for distalizing an upper molar (12) includes a main support shaft (50) disposed in the archwire receptacle (22) of a molar tooth bracket (20). A slide shaft (52) extends from the main support shaft (50) and movably supports a slide collar (56). The slide collar (56) is tied via a tensile ligature (66) to the bracket (34) of a secondary tooth (14), such as a premolar. A biocompatible and corrosion resistant compression spring (64) is operatively disposed between the slide collar (56) and the slide shaft (52). The compression spring (64) is prevented from buckling by a guide pin (60) extending centrally through the compression spring (64). The guide pin (60) is attached at one end to the slide collar (56) and the other end passes through a guide tube (58) extending rigidly from the slide shaft (52). A mesial support ligature (68) extends between the slide collar (56) and an archwire (38) to prevent inadvertent dislocation of the appliance (10).

28 Claims, 2 Drawing Sheets

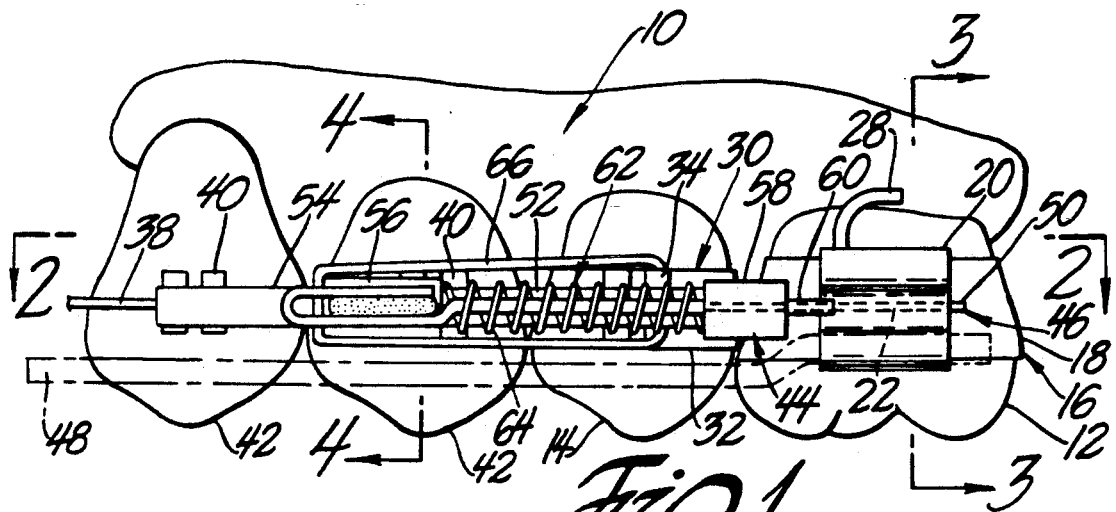
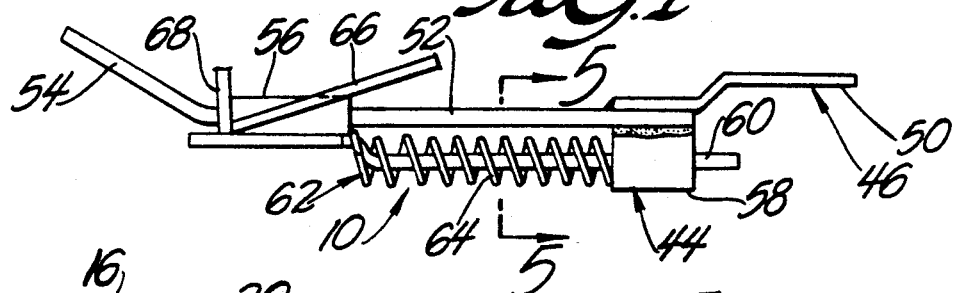
Fig. 1
Fig. 2
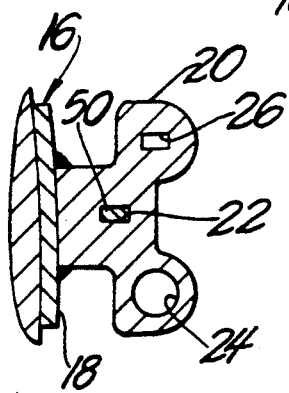
Fig. 3
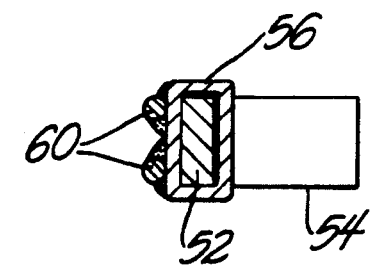
Fig. 4
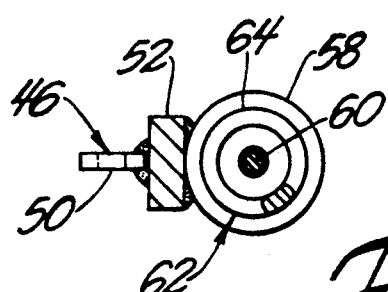
Fig. 5

ORTHODONTIC APPLIANCE

TECHNICAL FIELD

The subject invention relates to an orthodontic appliance, and more specifically, to a distalizing appliance for forcibly displacing a tooth.

BACKGROUND ART

Orthodontics is the branch of dentistry concerned with correcting and preventing irregularities of the teeth and poor occlusion. During orthodontic treatments, teeth are fitted with braces and moved into proper alignment, etc., by forcibly controlling movement of the teeth with the brace hardware and various appliances. Frequently, during the orthodontic treatment, it is necessary to distalize a primary tooth, e.g., an upper molar relative to a secondary tooth, e.g., a premolar or bicuspid. Such distalization of the primary tooth creates space between the two teeth, and more importantly moves the primary tooth into a desired posterior position.

Distalizing appliances for moving the primary tooth relative to a second tooth are known in the art. For example, head gear is perhaps the best known such orthodontic appliances for distalizing a primary tooth relative to the secondary tooth. With head gear, the orthodontic bracket fitted to the upper molar brace is provided with a head gear tube. The head gear wire is inserted into the head gear tube and tensile forces are exerted on the head gear wire by a strap extending behind the patient's neck. Head gear are extremely effective in distalizing the upper molars, however are plagued with certain disadvantages. For example, the head gear apparatus is traditionally uncomfortable, causing discomfort to the patient's neck and sometimes mouth. Further, head gear can be unsightly due to the external components. Also, and most importantly, the use of head gear requires patient cooperation. Thus, if the patient declines to wear the head gear appliance because of comfort, or concern for appearance, the upper molars will not be distalized.

Other orthodontic appliances have been proposed as an alternative to such head gear. For example, U.S. Pat. No. 4,595,361 to Blechman et al, issued Jun. 17, 1986, discloses an orthodontic appliance including repelling magnets disposed between the primary and secondary teeth for distalizing the primary tooth. In each of the several embodiments disclosed in Blechman et al, one magnet is supported in a head gear tube in the bracket of the primary tooth brace. For this reason, additional orthodontic appliances cannot be used on the primary tooth at the same time as the Blechman et al appliance. Accordingly, the Blechman et al appliance cannot be used simultaneously with head gear to further accelerate distalization of the primary tooth.

Another example of a molar distalizing appliance may be had in U.S. Pat. No. 5,064,370 to Jones, issued Nov. 12, 1991. The Jones patent discloses a compression spring distalizing appliance in lieu of the Blechman et al magnets. The bracket on the primary tooth brace includes a head gear tube and a standard archwire receptacle fixedly supported thereon. The compression spring of the distalizing appliance is carried on a main support shaft which engages the primary tooth brace through both the head gear tube and the archwire receptacle. In other words, all available tubes and/or receptacles in the bracket of the primary tooth brace are employed during treatment with the Jones appliance. Therefore, additional appliances, such as head gear, cannot be used simultaneously with the Jones distalizing appliance.

SUMMARY OF THE INVENTION AND ADVANTAGES

The subject invention contemplates an orthodontic appliance for distalizing a primary tooth, such as an upper molar. The appliance comprises a primary brace means for fixed attachment to a primary tooth. A central archwire receptacle is provided in the primary brace means. A secondary brace means is included for fixed attachment to a secondary tooth adjacent the primary tooth. A distalizer means is operatively disposed between the primary brace means and the secondary brace means for forcibly distalizing the primary brace means relative to the secondary brace means. A primary support means extends between the distalizer means and the primary brace means for engaging the primary brace means exclusively within the archwire receptacle thereby unencumbering any additional receptacles in the primary brace means to attach further orthodontic appliances.

The primary support means of the subject invention extends from the distalizer means and attaches to the primary brace means only in the archwire receptacle. Therefore, if the primary brace means further includes a head gear tube, that head gear tube will remain open even with the distalizer means operatively connected such that head gear can be worn simultaneously with the distalizer means of the subject invention. Thus, the primary tooth can be distalized or moved in some other manner at a much more rapid rate than heretofore available with the prior art distalizing appliances since, according to the subject invention, the distalizer means is supported exclusively within the archwire receptacle, thereby unencumbering a head gear tube (if any) and any other auxiliary tubes. Conversely, if no head gear tube or auxiliary tube is present, the distalizer means can still be used effectively by way of the archwire receptacle connection, where prior art appliances can not be used at all.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a front view of the subject orthodontic appliance operatively disposed upon the teeth;

FIG. 2 is a top view of the appliance as taken generally along lines 2—2 of FIG. 1;

FIG. 3 is a cross-sectional view of the primary tooth bracket as taken generally along lines 3—3 of FIG. 1;

FIG. 4 is a cross-sectional view of the distalizer means taken generally along lines 4—4 of FIG. 1;

FIG. 5 is a cross-sectional view of the distalizing means taken generally along lines 5—5 of FIG. 2;

DETAILED DESCRIPTION OF THE PREFERRED EMBODIMENT

Referring to the figures, wherein like numerals indicate like or corresponding parts throughout the several views, an orthodontic appliance according to the subject invention is generally shown at 10. The appliance 10 is of the type for distalizing a primary tooth 12, such as an upper molar, relative to a secondary tooth 14, such as a premolar or bicuspid.

Figure 7:
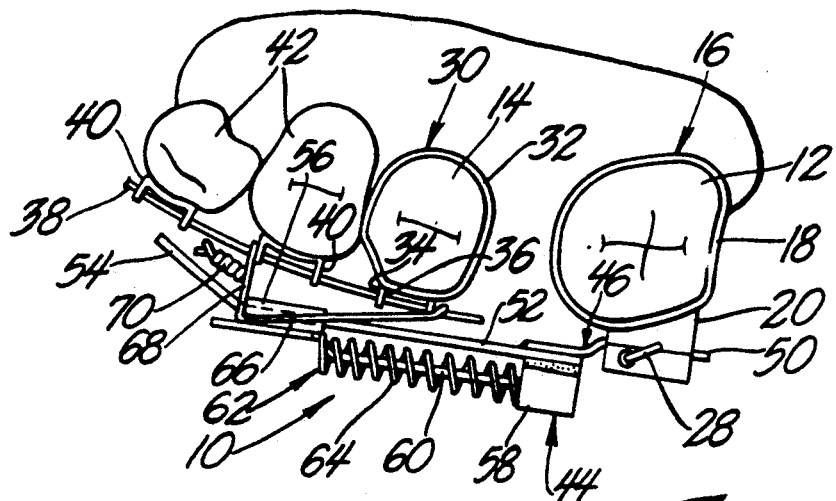
FIG. 7 is a bottom view of the orthodontic appliance as in FIG. 6 showing the primary tooth distalized and the compression spring fully expanded.
Figure 6:
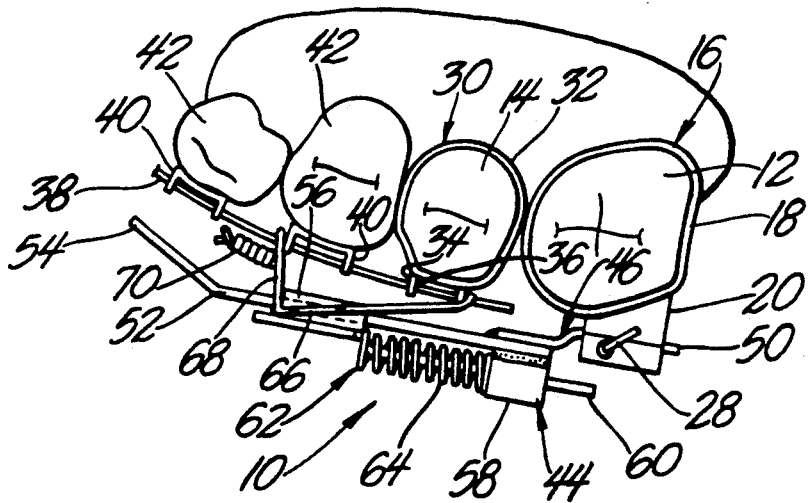
FIG. 6 is a bottom view of the orthodontic appliance as initially installed upon the patient's teeth, with the compression spring fully activated.

The appliance 10 includes a primary brace means, generally indicated at 16 in FIGS. 1, 6 and 7, for fixed attachment to the primary tooth 12. In typical fashion, however in no way imperative, the primary brace means 16 includes a metallic band 18 surrounding and cemented to the primary tooth 12, with a bracket 20 extending outwardly from the band 18. Alternatively, although not shown, the bracket 20 can be cemented directly to the surface of the primary tooth 12. As best shown in FIGS. 1 and 3, the bracket 20 includes a central archwire receptacle 22, a head gear tube 24 occlusally adjacent to and larger than the archwire receptacle 22, and an auxiliary tube 26 gingivally adjacent to the archwire receptacle 22. An interiorly extending hook 28 projects gingivally from the bracket 20. Referring to FIG. 3, the cross-sectional shape of the archwire receptacle 22 is shown to be generally rectangular, and likewise the auxiliary tube 26. The head gear tube 24, however, is generally circular cross section and significantly larger than the archwire receptacle 22.

A secondary brace means, generally indicated at 30 in FIGS. 1, 6 and 7 is provided for fixed attachment to the secondary tooth 14, which is adjacent the primary tooth 12. The secondary brace means 30 includes a band 32 surrounding the secondary tooth 14, and a bracket 34 extending outwardly from the band 32. Alternatively, although not shown, the bracket 34 can be cemented directly to the surface of the secondary tooth 14. The bracket 34 is provided with an archwire receptacle 36 for receiving a standard archwire 38.

In typical fashion, the archwire 38 is received laterally into the archwire receptacle 36 of the secondary brace means 30, with a band or metallic wire secured over the bracket 34 to retain the archwire 38 in the receptacle 36. However, the archwire 38 is received axially, or lengthwise, into the archwire receptacle 22 of the primary brace means 16. As best shown in FIGS. 6 and 7, the archwire 38 is connected to the brackets 40 extending from the face of the adjacent teeth 42. However, the archwire 38 terminates posterior the secondary brace means 30 for reasons to be described subsequently.

Distalizer means, generally indicated at 44, is operatively disposed between the primary brace means 16 and the secondary brace means 30 for forcibly distalizing the primary brace means 16 relative to the secondary brace means 30. That is, the distalizer means 44 reacts against the primary brace means 16 to force the primary tooth 12 rearwardly, or posteriorly, while preferably maintaining the secondary brace means 30 and in the secondary tooth 14 in a stationary position.

Primary support means, generally indicated at 46, extends between the distalizer means 44 and the primary brace means 16 for engaging the primary brace means 16 exclusively within the archwire receptacle 22 thereby unencumbering the additional head gear tube 24 and auxiliary tube 26 so that further orthodontic appliances may be attached to the primary base means 16. Accordingly, a standard head gear appliance, as illustrated in phantom at 48 in FIG. 1, can be worn simultaneously with the distalizer means 44 to further and more rapidly distalize the primary tooth 12. In like manner, other types of orthodontic appliances may be attached to the molar bracket 20, e.g., via the auxiliary tube 26 and/or the hook 28, simultaneously with the distalizer means 44 and a head gear appliance 48.

The primary support means 46 includes a main support shaft 50 having a generally rectangular cross-section. Ideally, the main support shaft 50 is fabricated from the same material as the archwire 38, with both members having the same cross-sectional configuration. The main support shaft 50 is fixedly connected, such as by brazing, to the distalizer means 44 and extends therefrom in offset fashion for insertion snugly within the archwire receptacle 22 of the primary brace means 16. The distalizer means 44 further includes a slide shaft 52 fixed to the main support shaft 50 by any well known means, such as soldering, brazing, welding or cementing. The slide shaft 52 is of metallic construction having a generally flat, elongated rectangular cross section as shown in FIG. 4. The slide shaft 52 includes a distal end having a mesial dog leg bend 54 to prevent lip and cheek irritation. A slide collar 56 is slideably disposed on the slide shaft 52 between the dog leg 54 and the connection at the main support shaft 50.

A guide tube 58 is fixedly connected to the slide shaft 52 and the main support shaft 50 adjacent the connection therebetween. An elongated metallic guide pin 60 extends from the slide collar 52 and is slideably disposed through the guide tube 58. Thus, as the slide collar 56 moves along the slide shaft 52, the guide pin 60 slides within the guide tube 58. As best shown in FIG. 5, the guide pin 60 has a circular cross-section.

Biasing means, generally indicated at 62 in FIGS. 1, 2, 5, 6 and 7, is operatively disposed between the main support shaft 50 and the slide collar 56 for biasing the primary brace means 16 toward the desired distalized position. The biasing means 62, more particularly, comprises a compression spring 64 disposed between the slide collar 56 and the guide tube 58. The compression spring 64 is coiled around the guide pin 60 so as to prevent buckling. Preferably, the compression spring 64 is fabricated from a nickel-titanium alloy, however stainless steel or other corrosion resistant and biocompatible materials may be used.

In order to prevent excessive bending moments applied to the main support shaft 50, a tensile ligature 66 extends from the distalizer means 44 and operatively engages the secondary brace means 30. That is, as best shown in FIGS. 1, 2, 6 and 7, the tensile ligature 66 extends around the slide shaft 52 and over the slide collar 56 and then loops rearwardly about the archwire 38 and the bracket 34 in the secondary brace means 30. By tightly drawing the tensile ligature 66, the compression spring 64 is activated or compressed to apply a distalizing force against the primary brace means 16, as best shown in FIG. 6.

To further prevent displacement of the distalizer means 44, a mesial support ligature 68 extends from the distalizer means 44 and is fixed relative to archwire 38. As perhaps best shown in FIGS. 6 and 7, the tensile ligature 66 and the mesial support ligature 68 are preferably formed of a single continuous wire strand which is first looped and twisted to form the tensile ligature 66 and then immediately feed around the archwire 38 and twisted to form a twisted end 70. The twisted end 70 of the mesial support ligature 68 is preferably tucked between the dog leg 54 of the slide shaft 52 and the archwire 38 to prevent gum or cheek irritation. The mesial support ligature 68 is required in the preferred embodiment due to the relatively thin main support shaft 50 engaged only in the archwire receptacle 22 of the primary brace means 16. Thus, when the patient is chewing food or some other external force is applied laterally to the distalizer means 44, the mesial support ligature 68, as well as a tensile ligature 66 and the main support shaft 50 prevent inadvertent displacement of the appliance 10.

The subject appliance 12 is installed simply by feeding the main support shaft 50 into the rectangular archwire receptacle 22 of the primary brace means 16. Accordingly, to provide clearance for the main support shaft 50, the archwire 38 is severed immediately behind the secondary brace means 30, as shown in FIGS. 6 and 7. Frequently, the primary brace means 16 is formed on a molar tooth 12, such that the primary brace means 16 is also fitted with a head gear tube 24 and possibly an auxiliary tube 26 for attaching additional orthodontic appliances. The distalizing means 44 is connected to the primary brace means 16 so that the head gear tube 24 and the auxiliary tube 26 remain unobstructed to receive additional orthodontic appliances, such as a head gear apparatus 48, which may be employed simultaneously with the distalizer means 44.

To activate the distalizer means 44, a thin malleable wire is looped around the archwire 38 and the bracket 34 of the secondary brace means 30 and then extended and twisted over the slide collar 56 and the slide shaft 52 in a tightening manner so as to activate, or compress, the compression spring 64. The same wire forming the tensile ligature 66 is then wrapped around the archwire 38 next to one of the adjacent teeth 42 with the ends of the wire tied off along a twisted end 70, as shown in FIG. 6.

As shown in FIG. 7, the distalizer means 44 applies a rearward, or posterior distalizing force against the primary tooth 12 so that the primary tooth 12 is distalized from the secondary tooth 14. In FIG. 7, the slide collar 56 is shown at its full length of travel by way of engagement with the dog leg 54, such that the primary tooth 12 will not be further distalized without reactivating the compression spring 54.

In order to reactivate the compression spring 64 from that shown in FIG. 7, the tensile ligature 66 and the mesial support ligature 68 are removed and discarded. A new malleable wire is looped and drawn around the bracket 34 of the secondary brace means 30 and the archwire 38, and then twisted and tightened around the slide shaft 52 and slide collar 56 in the same manner as discussed above, thereby compressing the compression spring 64. The wire is then looped around the archwire 38 to form the mesial support ligature 68 and tied off at the twisted end 70 thereby reactivating the distalizer means 16 to further forcibly urge the primary tooth 12 posteriorly in the mouth.

The primary advantage of the subject invention resides in the solitary, or exclusive and independent support of the distalizer means 44 within the archwire receptacle 22 of the primary brace means 16, thereby leaving open and unencumbered the head gear tube 24 and the auxiliary tube 26, as well as the hook 28. Thus, even with the distalizer means 44 in place, a head gear system 48 and any other appropriate orthodontic appliance connected to either the auxiliary tube 26 or the hook 28 may be simultaneously employed to further and more rapidly move the teeth into proper occlusal alignment.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An orthodontic appliance (10) for distalizing a primary tooth (12) such as an upper molar, said appliance comprising: primary brace means (16) for fixed attachment to a primary tooth (12) and including a central archwire receptacle (22) having an interior wall configuration; secondary brace means (30) for fixed attachment to a secondary tooth (14) adjacent the primary tooth (12); distalizer means (44) operatively disposed between said primary brace means (16) and said secondary brace means (30) for forcibly distalizing said primary brace means (16) relative to said secondary brace means (30); and primary support means (46) extending between said distalizer means (44) and said primary brace means (16) for engaging said primary brace means (16) exclusively within said archwire receptacle (22) thereby unencumbering any additional receptacles (24, 26) in said primary brace means (16) to attach further orthodontic appliances (48), said primary support means (46) having a cross-sectional shape irrotatably engaging said interior wall configuration of said archwire receptacle (22).

2. An appliance as set forth in claim 1 wherein said support means (46) comprises a main support shaft (50) having a generally rectangular cross section.

3. An appliance as set forth in claim 2 further comprising a tensile ligature (66) extending from said distalizer means (44) and operatively engaging said secondary brace means (30).

4. An appliance as set forth in claim 3 wherein said secondary brace means (30) includes an archwire receptacle (36), further comprising an archwire (38) disposed in said archwire receptacle (36) of said secondary brace means (30).

5. An appliance as set forth in claim 4 further comprising a mesial support ligature (68) extending from said distalizer means (44) and fixed relative to said archwire (38).

6. An appliance as set forth in claim 5 wherein said distalizer means (44) includes a slide shaft (52) fixed to said main support shaft (50).

7. An appliance as set forth in claim 6 further comprising a slide collar (56) slideably disposed on said slide shaft (52) and operatively connected to said tensile ligature (66).

8. An appliance as set forth in claim 7 further comprising biasing means (62) operatively disposed between said main support shaft (50) and said slide collar (56) for biasing said primary brace means (16) toward a desired distalized position.

9. An appliance as set forth in claim 8 further comprising a guide tube (58) fixedly connected to said slide shaft (52) and said main support shaft (50).

10. An appliance as set forth in claim 9 wherein said biasing means comprises a compression spring (64) disposed between said slide collar (56) and said guide tube (58).

11. An appliance as set forth in claim 10 further comprising a guide pin (60) extending from said slide collar (56) and slideably disposed through said guide tube (58) and said compression spring (54).

12. An appliance as set forth in claim 11 wherein said guide pin (60) has a circular cross section.

13. An appliance as set forth in claim 10 wherein said compression spring (64) is fabricated from a nickel-titanium alloy.

14. An appliance as set forth in claim 6 wherein said slide shaft (52) has a generally flat, elongated rectangular cross section.

15. An orthodontic appliance (10) for distalizing a primary tooth (12), such as an upper molar, said appliance comprising: primary brace means (16) for fixed attachment to a molar tooth (12), said primary brace means (16) having a central archwire receptacle (22) and a head gear tube (24) adjacent to and larger than said archwire receptacle (22); secondary brace means (30) for fixed attachment to a secondary tooth (14) adjacent the primary tooth (12); distalizer means (44) operatively disposed between said primary brace means (16) and said secondary brace means (30) for forcibly distalizing said primary brace means (16) relative to said secondary brace means (30); and primary support means (46) extending between said distalizer means (44) and said primary brace means (16) for reception within said archwire receptacle (22) while said head gear tube (24) remains unobstructed to receive an additional orthodontic appliance (48) simultaneously with said distalizer means (44).

16. An appliance as set forth in claim 15 wherein said primary support means (46) comprises a main support shaft (50) having a generally rectangular cross section.

17. An appliance as set forth in claim 15 further comprising a tensile ligature (66) extending from said distalizer means (44) and operatively engaging said secondary brace means (30).

18. An appliance as set forth in claim 17 wherein said secondary brace means (30) includes an archwire receptacle (36), further comprising an archwire (38) disposed in said archwire receptacle (36) of said secondary brace means (30).

19. An appliance as set forth in claim 18 further comprising a mesial support ligature (68) extending from said distalizer means (44) and fixed relative to said archwire (38).

20. An appliance as set forth in claim 19 wherein said primary support means (46) includes a main support shaft (50) and said distalizer means (44) includes a slide shaft (52) fixed to said main support shaft (50).

21. An appliance as set forth in claim 20 further comprising a slide collar (56) slideably disposed on said slide shaft (52) and operatively connected to said tensile ligature (66).

22. An appliance as set forth in claim 21 further comprising biasing means (62) operatively disposed between said main support shaft (50) and said slide collar (56) for biasing said primary brace means (16) toward a desired distalized position.

23. An appliance as set forth in claim 22 further comprising a guide tube (58) fixedly connected to said slide shaft (52) and said main support shaft (50).

24. An appliance as set forth in claim 23 wherein said biasing means (62) comprises a compression spring (64) disposed between said slide collar (56) and said guide tube (58).

25. An appliance as set forth in claim 24 further comprising a guide pin (60) extending from said slide collar (56) and slideably disposed through said guide tube (58) and said compression spring (64).

26. An appliance as set forth in claim 25 wherein said guide pin (60) has a circular cross section.

27. An appliance as set forth in claim 24 wherein said compression spring (64) is fabricated from a nickel-titanium alloy.

28. An appliance as set forth in claim 20 wherein said slide shaft has a generally flat, elongated rectangular cross section.

* * * * *